(12) United States Patent
Carroll (10) Patent No.: US 6,327,335 B1
(45) Date of Patent: Dec. 4, 2001

(54) APPARATUS AND METHOD FOR THREE-DIMENSIONAL IMAGING USING A STATIONARY MONOCHROMATIC X-RAY BEAM

(75) Inventor: Frank Carroll, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/290,436

(22) Filed: Apr. 13, 1999

(51) Int. Cl.$^7$ .............................. G01N 23/20; G21K 1/00
(52) U.S. Cl. .................. 378/85; 378/84; 378/36; 378/37
(58) Field of Search .................. 378/84, 87, 88, 378/86, 73, 43, 45, 49, 145, 37, 36, 85; 356/345, 350, 359, 360

(56) References Cited

U.S. PATENT DOCUMENTS

| | | |
|---|---|---|
| 3,381,127 * | 4/1968 | Momose .................................. 378/37 |
| 3,576,997 | 5/1971 | Slavin . |
| 3,772,522 | 11/1973 | Hammond et al. ................... 250/503 |
| 3,777,156 | 12/1973 | Hammond et al. . |
| 4,010,370 | 3/1977 | LeMay . |
| 4,037,920 | 7/1977 | Runciman et al. ....................... 350/7 |
| 4,082,416 | 4/1978 | Runciman et al. . |
| 4,082,417 | 4/1978 | Runciman et al. . |
| 4,118,099 | 10/1978 | Weiss et al. ......................... 350/3.73 |
| 4,132,654 | 1/1979 | Braun . |
| 4,144,457 | 3/1979 | Albert . |
| 4,149,076 | 4/1979 | Albert . |
| 4,179,100 | 12/1979 | Sashin et al. . |
| 4,203,034 | 5/1980 | Carroll, Jr. . |
| 4,210,810 | 7/1980 | Berry et al. . |
| 4,298,800 | 11/1981 | Goldman . |
| 4,311,389 | 1/1982 | Fay et al. . |
| 4,342,914 | 8/1982 | Bjorkholm . |
| 4,441,809 | 4/1984 | Dudley et al. . |
| 4,598,415 | 7/1986 | Luccio et al. . |
| 4,599,741 | 7/1986 | Wittry ..................................... 378/85 |
| 4,809,309 | 2/1989 | Beekmans . |
| 4,953,188 | 8/1990 | Siegel et al. . |
| 4,958,363 | 9/1990 | Nelson et al. ......................... 378/85 |
| 4,975,917 | 12/1990 | Villa . |
| 5,011,245 | 4/1991 | Gibbs . |
| 5,125,019 | 6/1992 | Evain et al. . |
| 5,132,997 | 7/1992 | Kojima et al. . |
| 5,138,642 | 8/1992 | McCroskey et al. . |
| 5,227,733 | 7/1993 | Yamada . |
| 5,245,648 | 9/1993 | Kinney et al. . |
| 5,247,562 | 9/1993 | Steinbach . |
| 5,263,073 | 11/1993 | Feldman . |
| 5,268,951 | 12/1993 | Flamholz et al. ...................... 378/34 |
| 5,268,954 | 12/1993 | Middleton . |
| 5,315,375 | 5/1994 | Allen . |
| 5,353,291 | 10/1994 | Sprangle et al. . |
| 5,479,017 | 12/1995 | Yamada et al. . |
| 5,495,515 | 2/1996 | Imasaki . |
| 5,509,043 | 4/1996 | Van Der Sluis ....................... 378/85 |
| 5,541,944 | 7/1996 | Neil . |

(List continued on next page.)

Primary Examiner—Drew Dunn
(74) Attorney, Agent, or Firm—Cooley Godward, LLP (57) ABSTRACT

A three-dimensional imaging device comprising a stationary monochromatic beam source projecting a beam onto a plurality of reflective mosaic crystals, wherein the plurality of mosaic crystals reflect the beam through a stationary object onto a stationary detector. A way for scanning the object includes moving the entire set of the mosaic crystals linearly along a line in the plane of the crystals, and rotating the entire plurality of crystals about an axis through the stationary beam source while maintaining the plurality of crystals in a fixed relative orientation. A potential application of the invention is to improve the accuracy of mammography in the diagnosis of breast cancer.

45 Claims, 6 Drawing Sheets

U.S. PATENT DOCUMENTS

| | | |
|---|---|---|
| 5,602,894 | 2/1997 | Bardash . |
| 5,604,782 | 2/1997 | Cash, Jr. ............................. 378/85 |
| 5,628,314 | 5/1997 | Kumagai ........................ 128/653.1 |
| 5,781,606 | 7/1998 | Dobbs et al. . |
| 5,805,620 | 9/1998 | Liu et al. . |
| 5,815,517 | 9/1998 | Ikegami . |
| 5,825,847 | 10/1998 | Ruth et al. . |
| 5,850,425 | * 12/1998 | Wilkins ............................. 378/85 |
| 5,881,126 | * 3/1999 | Momose ............................ 378/36 |
| 5,930,325 | * 7/1999 | Momose ............................ 378/37 |
| 6,023,496 | * 2/2000 | Kuwabara ......................... 378/85 |
| 6,108,397 | * 8/2000 | Cash, Jr. ............................ 378/85 |
| 6,128,364 | * 10/2000 | Niemann ........................... 378/85 |
| 6,195,410 | * 2/2001 | Cash, Jr. ............................ 378/85 |

\* cited by examiner

APPARATUS AND METHOD FOR THREE-DIMENSIONAL IMAGING USING A STATIONARY MONOCHROMATIC X-RAY BEAM

ACKNOWLEDGEMENTS

This invention was made with government support under Grant No. N00014-99-1-904 awarded by the Office of Naval Research. The U.S. Government has certain rights in the invention as a result of this support.

BACKGROUND OF THE INVENTION

The present invention relates generally to a three-dimensional x-ray imaging device. More particularly, this invention pertains to a mosaic crystal imaging device for three-dimensional acquisition and reconstruction of radiographic information with a stationary monochromatic x-ray beam, stationary object, and stationary detector. One important application of the invention is in improving the accuracy of mammography in the diagnosis of breast cancer.

The present invention was developed to overcome the deficiencies inherent in two-dimensional imaging of cancerous tumors and tissues. The present invention is directed towards the development of improved sensitivity and specificity in monochromatic x-ray imaging. Using standard x-ray techniques, the three-dimensional information characterizing an object is displayed as a planar two-dimensional image on the film or flat imaging plane. Using conventional imaging techniques, a small area of dense tumor would image the same as larger amounts of less dense normal tissue on standard films. To obtain a three-dimensional view of the target object using prior art methods, one would need to move the x-ray beam, the object, and/or the detector to gain the additional spatial information concerning the tissue, such as in CT or standard tomography. Because the x-ray beam cannot always be moved, the present apparatus and method was devised for x-ray beam rotation using mosaic crystals for stationary beam sources.

Prior art systems for x-ray imaging are shown in U.S. Pat. No. 3,772,522, issued to Hammond et al. on Nov. 13, 1993; U.S. Pat. No. 4,037,920, issued to Runciman et al. on Jul. 26, 1977; U.S. Pat. No. 4,118,099, issued to Weiss et al. on Oct. 3, 1978; U.S. Pat. No. 4,599,741, issued to Wittry on Jul. 8, 1986; U.S. Pat. No. 4,958,363, issued to Nelson et al. on Sep. 18, 1990; U.S. Pat. No. 5,262,951, issued to Flamholz et al. on Dec. 7, 1993; U.S. Pat. No. 5,509,043, issued to Van Der Sluis on Apr. 16, 1996; U.S. Pat. No. 5,628,314, issued to Kumagai on May 13, 1997; and U.S. Pat. No. 5,604,782, issued to Cash, Jr. on Feb. 18, 1997. Each of these patent disclosures is briefly outlined in the following discussion, and is hereby incorporated by reference.

U.S. Pat. No. 3,772,522, issued to Hammond et al. on Nov. 13, 1973, discloses a CRYSTAL MONOCHROMATOR AND METHOD OF FABRICATING A DIFFRACTION CRYSTAL EMPLOYED THEREIN. This specification teaches the use of a toroidal diffraction crystal with a curvature equal to the diameter of a Rowland circle. A monochromator is provided in which the diffraction crystal focuses x-radiation from a source at a point on the Rowland circle onto a target at a conjugate point on the Rowland circle.

U.S. Pat. No. 4,037,920, issued to Runciman et al. on Jul. 26, 1977, discloses a RADIATION SCANNING SYSTEM WITH TWO RELATIVELY MOVABLE REFLECTORS. This device teaches a radiation scanning system including two sets of planar reflective surfaces on which one set is movable relative to the other. A rotary assembly carrying one of the sets of planar reflective surfaces about an axis of rotation is also disclosed. A detector is arranged relative to an optical means such that the radiation enters the detector after sequential reflection from the reflective surfaces of the two sets.

U.S. Pat. No. 4,118,099, issued to Weiss et al. on Oct. 3, 1986, discloses IMAGE CODING AND DECODING USING COHERENT CODES. The disclosure teaches a laser, which may be monochromatic, split into two beams by semitransparent mirrors. The mirrors are shown at a common angle relative the source beam. The second mirror is at a spaced distance from the first mirror, wherein the spaced distance is in a direction perpendicular to the source beam. Additionally, the '099 patent teaches use of semitransparent reflective surfaces.

U.S. Pat. No. 4,599,741, issued to Wittry on Jul. 8, 1986, discloses a SYSTEM FOR LOCAL X-RAY EXCITATION BY MONOCHROMATIC X-RAYS. The patent teaches a system for x-ray fluorescence analysis which utilizes a plurality of parfocal diffractors to selectively monochromatize x-rays and focus them on a sample to be analyzed. Thus the '741 patent teaches use of rotating diffractive surfaces in conjunction with a stationary source and a stationary target. However, the diffractive surfaces are required to satisfy Johannson geometric conditions.

U.S. Pat. No. 4,958,363, issued to Nelson et al. on Sep. 18, 1990 discloses an APPARATUS FOR NARROW BANDWIDTH AND MULTIPLE ENERGY X-RAY IMAGING. The specification teaches a scanning system for dual energy imaging applications. The beam is scanned through a patient by means of adjusting the angle of incidence on a mirror.

U.S. Pat. No. 5,262,951, issued to Flamholz et al. on Dec. 7, 1993 discloses a X-RAY BEAM SCANNING METHOD FOR PRODUCING LOW DISTORTION OR CONSTANT DISTORTION IN X-RAY PROXIMITY PRINTING. The disclosure discusses a x-ray scanning method utilizing a pair of reflective mirrors to achieve a vertical scan (or a longitudinal scan through a patient). The mirrors may be moved linearly. The scan is used to etch a mask-wafer with low resultant distortion.

U.S. Pat. No. 5,509,043, issued to Van Der Sluis on Apr. 16, 1996 discloses an ASYMMETRICAL 4-CRYSTAL MONOCHROMATOR. This device teaches a x-ray analysis apparatus comprising a dispersion system of crystals for monochromatizing an incoming beam. It also teaches a means for rotating crystal pairs about an axis perpendicular to the axis of the incoming beam.

U.S. Pat. No. 5,628,314, issued to Kumagai on May 13, 1997 discloses MULTI-LASER BEAM-SCANNING THROUGH LIVING BODY PENETRATION DIAGNOSIS AND TREATMENT APPARATUS. The invention is centered around a diagnostic apparatus to obtain a laser fluorescent image. The '314 patent discloses use of mirrors to scan the laser beam parallel to a stationary patient and rotation of the laser source and mirrors, in a semi-fixed relation, to obtain stereographic imaging. The source and mirrors are referred to as being in semifixed relation, rather than fixed relation, because the mirrors move to effect the parallel scan.

U.S. Pat. No. 5,604,782, issued to Cash, Jr. on Feb. 18, 1997 discloses SPERICAL MIRROR GRAZING INCIDENCE X-RAY OPTICS. The patent teaches an optical system for x-rays combining at least two spherical mirrors for each dimension in grazing incidence orientation. Of relevance is that the '782 patent teaches an apparatus for reflecting two beams of x-ray radiation at a focal plane. See FIG. 6 of the '782 patent disclosure. The '782 patent uses at least 6 spherical mirrors, 3 per beam, and means for orienting the mirrors such that the beams graze off the respective mirrors in a manner so as to reduce the comatic aberration of extremum rays. It teaches orienting the mirrors to direct the X and Y coordinates of the beam.

The teachings of the prior art are limited in their applications and embodiments. The prior art does not teach an axis of rotation for reflective surfaces where the axis of rotation is concentric with the axis of the incoming x-rays. Nor does the prior art teach the use of multiple opaque surfaces for splitting a monochromatic x-ray beam into two x-ray beams. Furthermore, the prior art fails to teach the use of non-Johannson diffractive surfaces with a stationary source and target with a concentric axis of rotation for the surfaces.

An additional feature not taught in the prior art is the three dimensional scan of a patient by converging a split beam onto the object that is to be imaged with a beam detector. Finally, the prior art fails to teach the use of a split beam in a linear and rotational mirror device as a means for obtaining a three-dimensional image of an object.

What is needed, then, is an imaging device for three-dimensional acquisition and reconstruction of radiographic information using a stationary monochromatic x-ray beam to view a stationary object with a stationary detector.

SUMMARY OF THE INVENTION

The present invention is a three-dimensional imaging device comprising a stationary monochromatic beam source projecting a beam onto a plurality of reflective mosaic crystals, wherein the plurality of mosaic crystals reflect the beam through a stationary object onto a stationary detector. Means for scanning the object include moving the plurality of mosaic crystals linearly along a line in the plane of the crystals, and rotating the plurality of crystals about an axis through the stationary beam source while maintaining the plurality of crystals in a fixed relational orientation. A potential application of the invention is to improve the accuracy of mammography in the diagnosis of breast cancer.

DESCRIPTION OF THE PREFERRED EMBODIMENTS

Figure 1:
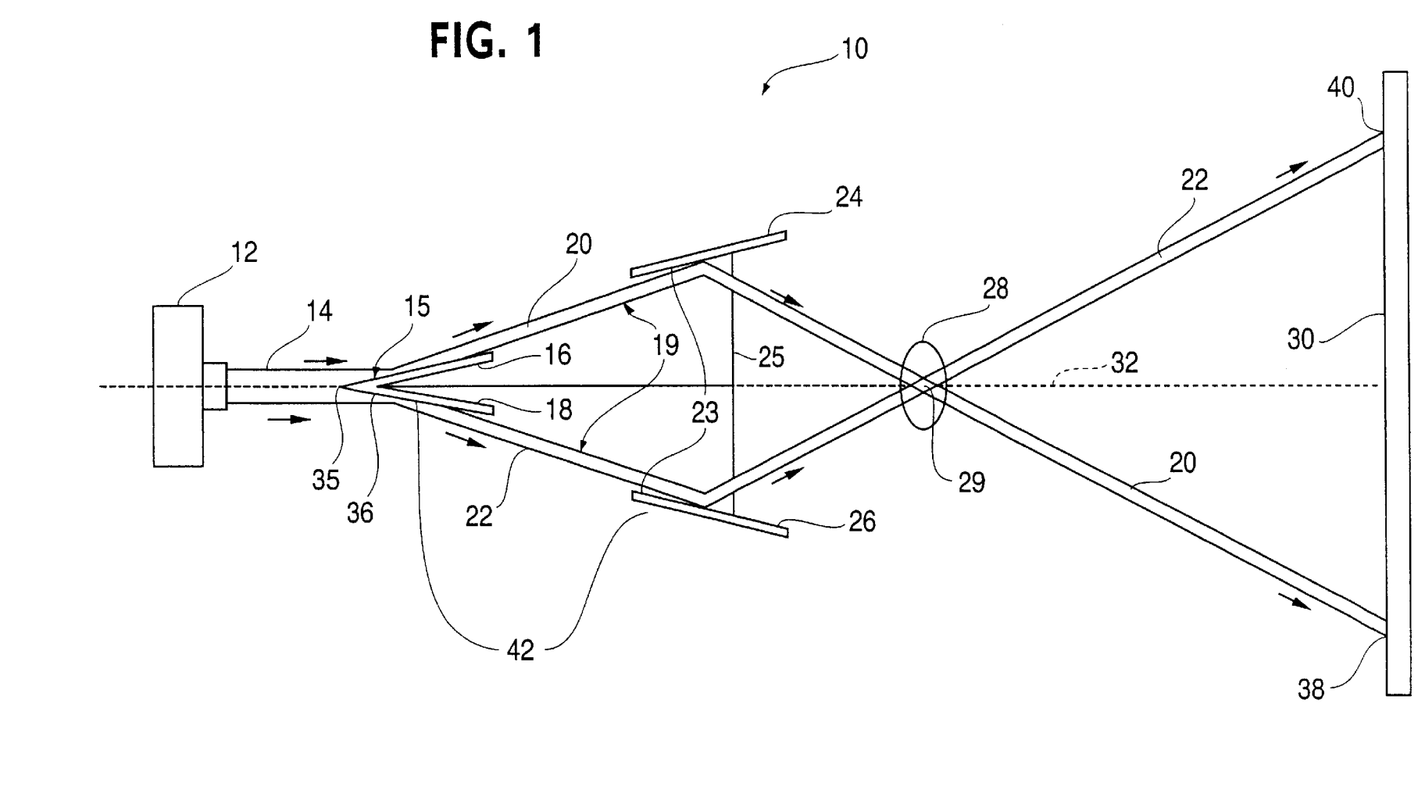
FIG. 1 is a schematic representation of the three-dimensional imaging apparatus of the present invention.

Overview:

As shown in FIG. 1 of the drawings, a three-dimensional imaging device 10 includes a stationary beam source 12 which projects a initial, first, alpha, primary X-ray beam 14. The alpha beam 14 is directed onto a set of mosaic reflective aiming crystals 15. The set of aiming crystals 15 re-directs alpha beam 14 to form a beta or second beam 19 that is aimed at a reflective mosaic steering crystal 23. The beta beam 19 is re-directed by the steering crystal 23 to pass through an object 28 and onto a detector 30. The steering crystal 23 and the aiming crystal 15 form a plurality of crystals 42 which is also known as a crystal set 42. This crystal set 42 can be linearly adjusted to reposition the beam 14 to allow for linear imaging of the object 28. The aiming crystal 15 and the steering crystal 23 are mounted on a frame 25 which can be rotated to produce a rotational imaging of the object 28. By combining the linear imaging and the rotational imaging of the object, a three dimensional image of the object 28 can be directed onto the detector 30.

Generation and Monocromatization of Beam:

As currently practiced, the alpha beam 14 is created by a stationary monochromatic beam source 12. One embodiment of the present invention is designed for use with a monochromatic x-ray beam generated by a Free Electron Laser (FEL). This monochromatic x-ray is to be delivered through a stationary beam pipe to an imaging lab on the floor above the FEL vault.

Another option would allow for a white x-ray beam to be input to device by relying on the crystal set 42 to create the monochromatic beam. In this manner, the invention can be used with any conventional source of x-rays, such as a standard mammography machine because the mosaic crystals will monochromatize any X-ray source to form a stationary monochromatic beam source 12. Thus, a standard x-ray machine may be used with mosaic crystals to form a stationary monochromatic beam source 12.

For the present embodiment, the alpha beam 14 was initiated by utilizing the output of a standard X-ray mammography unit (Philips Diagnostat) with a Kevex continuous wave Mo X-ray tube. This output is monochromatized by the mosaic crystals within the imaging device. The incoming x-ray beam is a polychromatic or white x-ray beam, which is then separated out into the monochromatic beam by the angle of contact with the mosaic crystals. By aligning the crystal to various orientations, different monochromatic beams may be reflected off of the mosaic crystals for imaging purposes. The tilt of the crystal controls the spectrum of the white x-ray beam that is reflected to create the monochromatic beam according to the Bragg angle.

The x-ray beam used in the present invention was designed to operate in the 14 kv to 18 kv range. However, it is also anticipated that x-ray beams in the 10 kv to 80 kv range could be used for imaging different parts of the human anatomy. This range of disclosures are meant for explaining the application and embodiment of the invention and are not meant to limit the range of use for this invention.

Splitting of Beam:

FIG. 1 of the drawings shows the set of mosaic reflective aiming crystals 15 which are also known as substantially-opaque reflective surfaces 15. While the invention may be used with only one aiming mirror and one steering mirror, the more complex method of utilizing multiple mirrors for splitting beams is described. This method utilizes the same principals as the single beam positioning, but also teaches a method for utilizing the more complex multiple beam arrangement.

The aiming crystals 15 are shown as a first reflective mosaic aiming crystal 16 and a second reflective mosaic aiming crystal 18. When multiple aiming crystals a re used, they can split the alpha beam 14 into multiple beta beams 19. The first aiming crystal 16 redirects a portion of the alpha beam 14 to form a first beta beam 20, and a s econd be am aiming crystal 18 redirects a separate portion of the alpha beam 14 to form a second beta beam 22. The first beta beam 20 and the second beta beam 22 form the set of multiple beta beams 19 that are divided from the alpha beam 14. Thus, the described construction forms a three-dimensional imaging device 10 that uses an alpha beam 14 that is split by multiple opaque reflective surfaces 15 into multiple beta beams 19.

While the present embodiment describes the system as using a first beta beam 20 and a second beta beam 22, it is also envisioned that the set of aiming crystals 15 could include any multiple of reflective crystal s to divide the alpha beam 14 into any number of multiple beta beams 19. It is also envisioned that a conical aiming crystal 15 could create a multiple beams in a circular pattern for imaging an object 28. This would eliminate the need to rotate the crystal set 42 to image the object 28.

The alpha beam 14 is split into a first beta beam 20 and a second beta beam 22 using two mosaic crystals 16 and 18 joined at the apex 35 of an inverted "V" 36. Each of these crystals 16 and 18 is angled approximately five (5) to seven (7) degrees off the central axis 32 of the alpha beam 14, depending upon the X-ray energy one wishes to select for imaging purposes. This effectively deflects approximately fifty percent (50%) of the x-rays falling on each crystal 16 and 18 into the first beta beam 20 and second beta beam 22 at a ten (10) degree angle from the central axis.

Aiming the Beam:

The set of multiple beta beams 19 is aimed by the set of aiming crystals 15 onto a set of reflective mosaic steering crystals 23. The set of steering crystals 23 is shown in FIG. 1 as a first steering crystal 24 and a second steering crystal 26. The first beta beam 20 is aimed by the first aiming crystal 16 at the first steering crystal 24, and the second beta beam 22 is aimed by the second aiming crystal 18 at the second steering crystal 26. Thus, a method for splitting an alpha beam 14 into multiple beta beams 19 is provided with a method for aiming the multiple beta beams 19 at a set of steering crystals 23.

In the preferred embodiment, the aiming crystals 15 are angled from the alpha beam at approximately five (5) degrees which allows for the beta beam 19 to be five (5) degrees off of the mirror orientation. This is transferred ,at a ten (10) degree angle, onto the steering crystals 23. The beta beam approaches and also leaves the steering crystal 24 at an angle of ten (10) degrees. Note that the second angle ten (10) degrees is twice that of the first angle five (5) degrees. In use and practice, the incoming angle of approximately five (5) to seven (7) degrees is appropriate for the current energy source being used. Thus, the steering crystal 23 orientation would be ten (10) to fourteen (14) degrees from the first beta beam.

Figure 8:
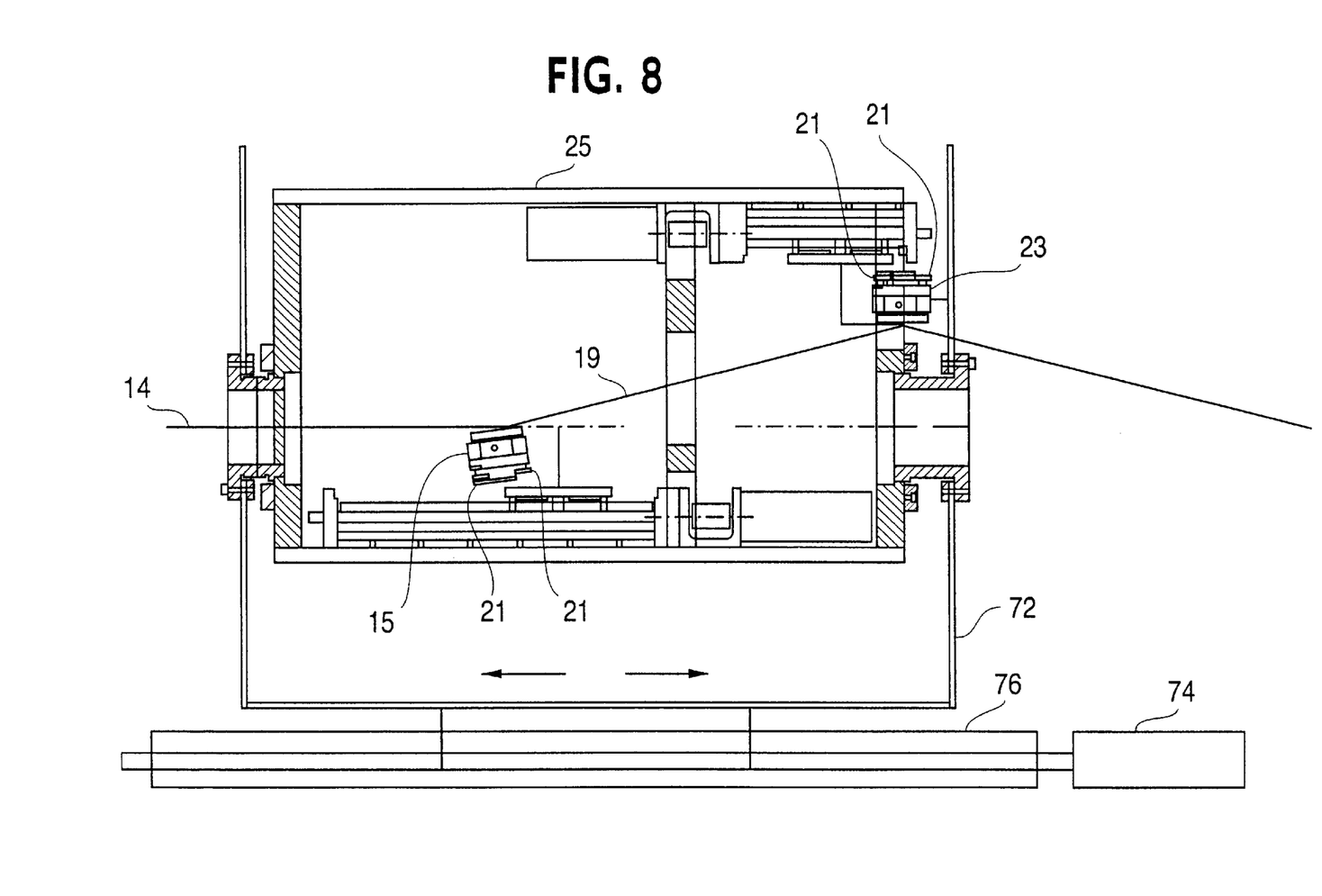
FIG. 8 is a schematic representation of the imaging device of the present invention.

As shown in FIG. 8, the positioning of each the crystals, including both the aiming crystals 15 and the steering crystals 23, is controlled by three (3) picomotors 21. These picomotors 21 are oriented to control the positioning of the associated crystal in three dimensions by controlling the angle and tilt of the crystal. One (1) picomotor 21 is located at the front of the crystal to control the front end vertical orientation and (2) two picomotors 21 are used on the back end of the crystal to control the left to right and vertical orientation of the back of the mosaic crystal mirror. Thus, these picomotors 21 control the altitude and tilt of each of the mosaic crystal mirrors.

Ideally, the steering mirrors or crystals 23 would be placed parallel to the initial beam 14, however, practice has shown that this is a theoretical position and that some adjustment is necessary. Therefore, the steering crystals 23 have also been mounted with the three (3) picomotors 21 to allow proper positioning of the steering crystals 23.

The length of distance between the first mirror and the second mirror is determined by the energy used and the size of the wave form that is to be used for the x-ray imaging.

Steering the Beam:

The multiple beta beams 19 are re-directed by the set of steering crystals 23 to pass through an object 28 and onto a detector 30. As shown in FIG. 1, the first steering crystal 24 re-directs the first beta beam 20 through the object 28 and onto the detector 30. In a similar manner, the second steering crystal 26 re-directs the second beta beam 22 through the object 28 and onto the detector 30. The multiple beta beams 19 are re-directed to converge at a converging location 29 in the object 28. In this manner, multiple images of the converging location 29 may be delivered to the detector 30 from the alpha beam 14.

The steering crystals 24 and 26 are set up to re-direct the first beam 20 and second beam 22 back at the object 28. The set of multiple beta beams 19 is re-directed at a twenty (20) degree angle from their approach to the set of steering crystals 23. Thus, the first and second beams 20 and 22 are first bounced at ten (10) degrees off of the aiming crystals 15 and then re-bounced using the twenty (20) degree bounce off of the set of steering crystals 23. This allows the first beam 20 and second beam 22 to converge at the object 28 from two different angles or locations.

Detecting the Beam:

The multiple beta beams 19 pass through the object 28 and onto the detector 30. As shown in FIG. 1, the first and second beta beams 20 and 22 pass through the object 28 creating images at a first detector position 38 and a second detector position 40. This method offers two different perspectives through the object 28. The detector 30 records the images of the object 28 transferred by the first beta beam 20 and the second beta beam 22. The first beta beam 20 passes through the object 28 and contacts the detector 30 at a first image location 38. The second beta beam 22 passes through the object 28 and contacts the detector 30 at a second image location 40. The first image location 38 and second image location 40 form a set of image locations 41 that may be used for analyzing the object 28. In this manner, multiple images may be recorded for an object from an alpha beam 14. The information gathered by the detector 30 can be used in conjunction with back-projection algorithms to reconstruct the three-dimensional internal anatomy of the object 28 that is being imaged.

Imaging by Positioning the Beam:

The three dimensional imaging device 10 provides a means for scanning the object 28 to provide an expanded two-dimensional image on the detector 30 of the three-dimensional object 28 that is being scanned. This means for scanning includes re-directing the set of beta beams 19 in two separate positioning movements to perform the three-dimensional scan. The first positioning movement is a linear positioning movement of the set of beta beams 19 by re-positioning the plurality of crystals 42. The second positioning movement is the rotational positioning movement of the set of beta beams 19 by rotating the plurality of crystals 42. By combining the linear positioning and the rotational positioning, the three-dimensional image information about the object 28 can be transferred onto the detector 30.

The explanations of the linear and rotational adjustments of the three dimensional imaging device 10 will be described using a discrete element time analysis for clarification purposes. However, it is also envisioned that the device 10 can perform a constantly adjusted sweep for imaging the complete device with a single extended burst of the alpha beam 14. Thus, the imaging device 10 can work in both: (1) a discrete imaging mode for individual pictures of different aspects of the object 28; and (2) a sweep mode whereby larger portions of the object 28 maybe viewed in a single extended burst of the alpha beam 14.

Figure 2:
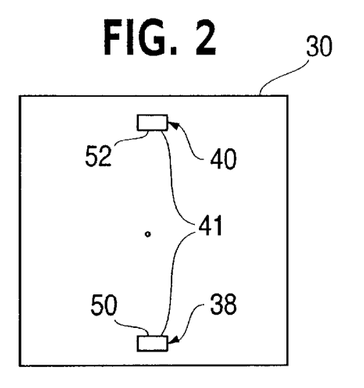
FIG. 2 is a schematic representation of a detector image.

Linear Positioning Movement:

FIG. 2 of the drawings shows a set of image locations 41 for a single burst of the alpha beam 14. The first image location 38 is shown as a first beam exposure 50 and the second image location 40 is shown as a second beam exposure 52. These exposures 50 and 52 are shown for a primary exposure time T1, and are shown as a portion of a segment on a detector 30.

Figure 3:
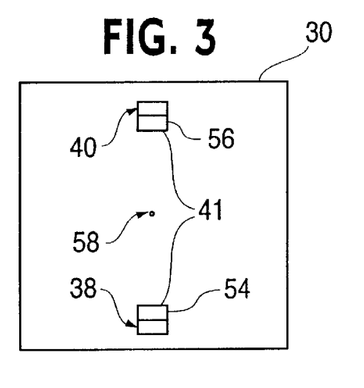
FIG. 3 is a schematic representation of the detector image of FIG. 2 after a linear repositioning of the three-dimensional imaging apparatus.

FIG. 3 of the drawings shows the next set image locations after a linear repositioning of the device 10. As noted in the change from FIG. 2 to FIG. 3 of the drawings, the linear adjustment of the set of steering crystals 23 not only changes the part of the object 28 that is being imaged, but also changes the location of the image on the detector 30. FIG. 3 of the drawings shows the position for an additional linear first beta beam exposure 54 and an additional linear second beta beam exposure 56 for a second time interval T2. These additional exposures 54 and 56 provide additional images of the object 28 after the set of beta beams 19 has been linearly repositioned. If a sweeping linear adjustment had been performed, then a single exposure area would cover the primary first and second beta beam exposures 50 and 52 and the additional first and second linear beta beam exposures 54 and 56. Thus, one can understand that the linear repositioning of the device adds a layer of information along a line in the plane of the detector 30 that crosses a central rotating point 58.

Figure 9A:
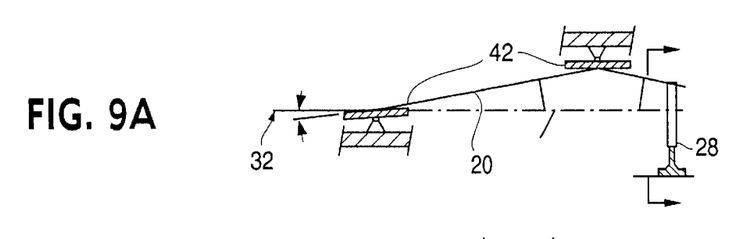
FIGS. 9a, 9b, 10a, 10b, 11a, 11b, 12a and 12b are schematic representations of a linear movement of the three-dimensional apparatus of the present invention.
Figure 9B:
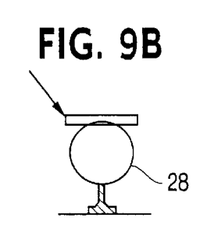
Figure 10A:
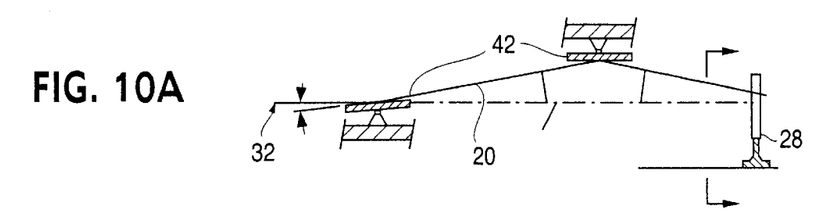
Figure 10B:
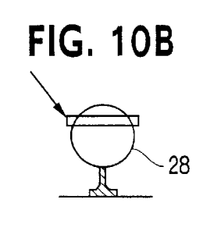
Figure 11A:
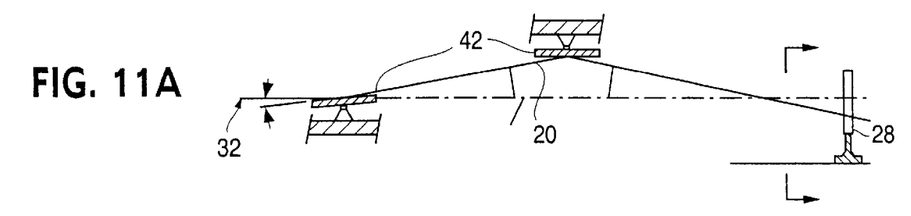
Figure 11B:
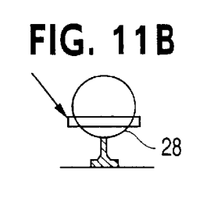
Figure 12A:
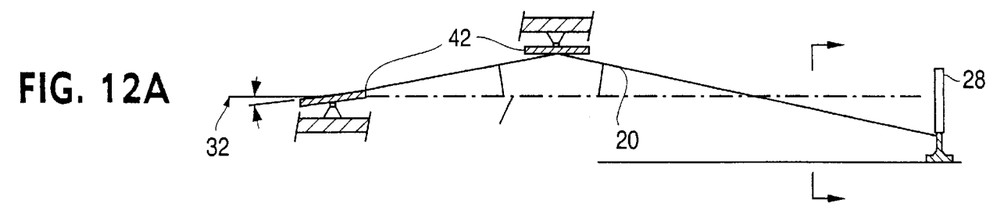
Figure 12B:
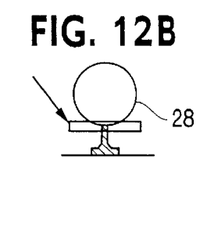

As shown in FIGS. 9a, 9b, 10a, 10b, 11a, 11b, 12a and 12b of the drawings, the linear positioning movement of the set of beta beams 19 is controlled by linearly moving the plurality of crystals 42. As shown in FIGS. 9a and 9b, when the plurality of crystals 42 is close to the object 28, then a first edge of the object 28 is being viewed. The plurality of crystals 42 can then be linearly adjusted along the axis, as represented by line 32, to properly position the first beta beam 20 on the next area of the object 28 that is to be monitored. This adjustment is shown in FIGS. 10a and 10b. FIGS. 11a and 11b and FIGS. 12a and 12b illustrate the continued linear movement and the associated scan of the object 28, until the entire object 28 has been scanned by the linear positioning of the plurality of crystals 42.

As noted above, the positioning of the entire crystal set 42 not only affects the area of the object 28 to be monitored, but also changes the position of the first and second image locations 38 and 40 on the detector 30. This method allows for multiple linear images of the object 28 to be transferred onto the detector 30.

It is important to realize that the actual shape of the set of image locations 41 will depend upon the shape, size, and type of alpha beam 14 and set of multiple beta beams 19 that are used. The preferred embodiment of this invention uses rectangular shaped beta beams for imaging the object 28, although it is also envisioned that other shapes could also be used. If the size of the scanning beam is sufficient to cover the object being imaged, then no linear movement of the imaging device 10 will be necessary.

The first embodiment of this invention used a rectangular shape of beam because of the flat type of mosaic crystal that was used. It is also envisioned that a bent or cylindrically arranged crystal could reflect a circular beam that could be used for imaging the object. If a large enough circular beam is used, then it is not necessary to linear position the x-ray mosaic imaging device because the circular beam will cover the entire shape of the object from each angular orientation.

As shown in FIG. 8 of the drawings, the crystal set 42 is mounted on a frame 25. The frame 25 is mounted on a structural support 72. The structural support 72 is positioned by linear stepping motor 74 with screw drive assembly 76 for moving the x-ray imaging apparatus in a linear manner to make a three dimensional scan of the object 28. It is also anticipated that the plurality of crystals 42 could be moved in a linear manner together by synchronizing the movement of both the aiming 15 and steering 23 mirrors. However, by moving the entire frame 25, a simpler method of realigning the linear position of the plurality of crystals 42 is formed.

Figure 4:
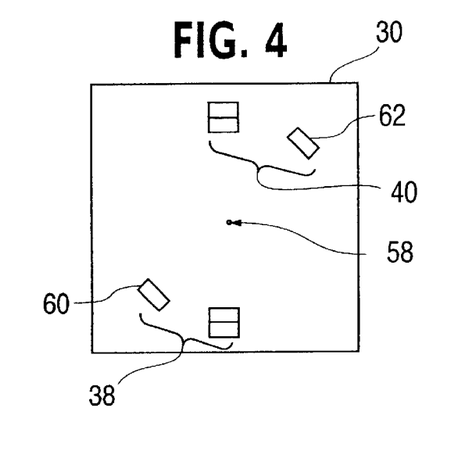
FIG. 4 is a schematic representation of the detector image of FIG. 3 after a rotational repositioning of the three-dimensional imaging apparatus.

Rotational Positioning Movement:

FIG. 4 of the drawings shows the position for the additional rotating first beta beam exposure 60 and the additional rotating second beta beam exposure 62 for the object 28 after the set of beta beams 19 have been rotationally repositioned from the exposure shown in FIG. 3. If a sweeping rotational adjustment had been performed, then a single exposure area would cover the exposures shown in FIG. 3 and the additional first and second rotational beta beam exposures 60 and 62. Thus, one can understand that the rotational repositioning of the device 10 adds a layer of information that is rotated about the central rotating point 58 on the detector 30.

The change from FIG. 3 to FIG. 4 of the drawings shows the rotational repositioning of the three-dimensional imaging device 10. The means for rotating the set of multiple beta beams 19 is provided by rotating both the set of aiming crystals 15 and the set of steering crystals 23 about the axis 32.

The set of aiming crystals 15 and the set of steering crystals 23 are mounted to form a crystal set 42. The crystal set 42 is also known as a plurality of crystals 42. This crystal set 42 is connected to a rotating frame 25 to allow the crystal set 42 to rotate through a full 360 degrees in front of the object 28. This allows the crystal set 42 to rotate in a coronal plane to collect information about the object 28 on the detector 30.

Figure 13:
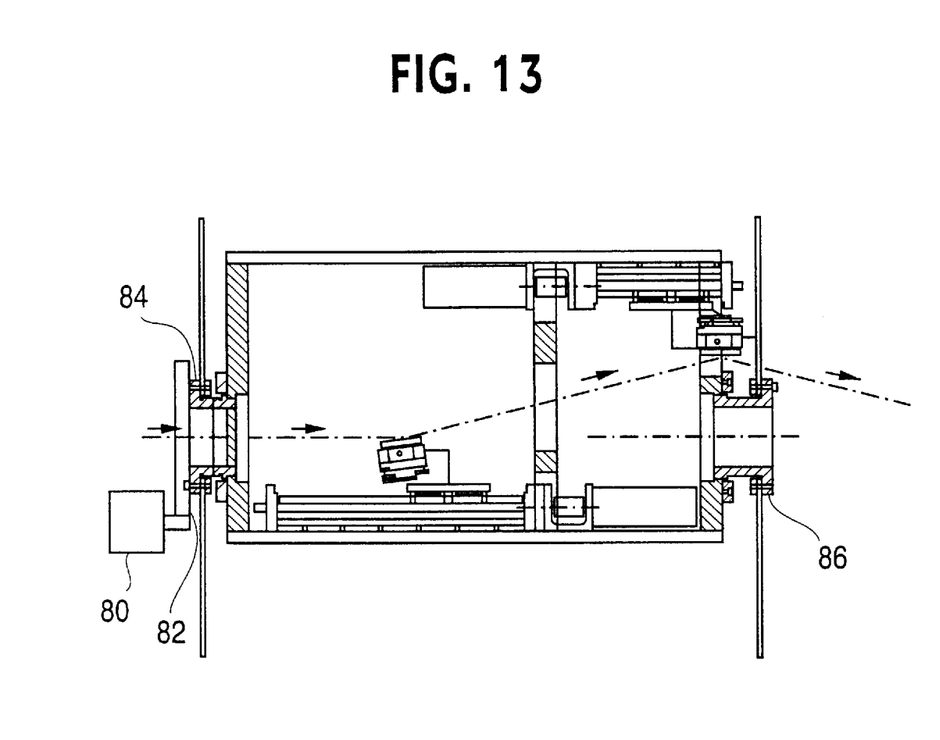
FIG. 13 is a schematic representation of the imaging device of the present invention.
Figure 14:
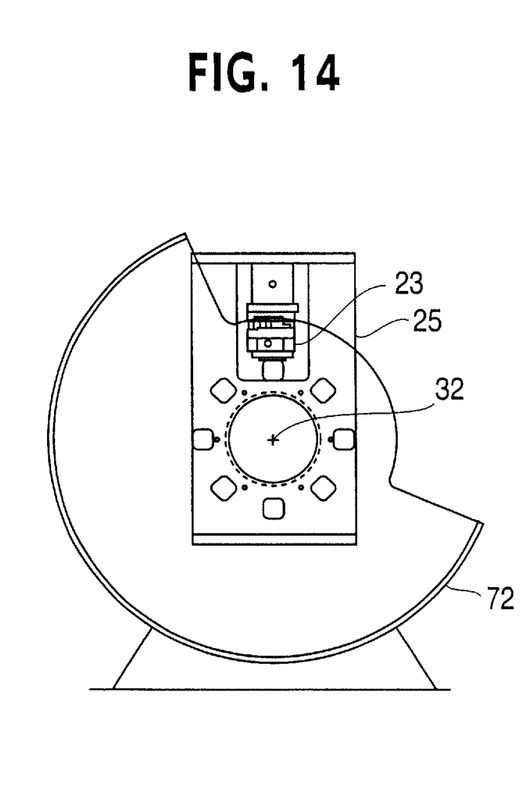
FIGS. 14–17 are schematic representations of a rotational movement of the three-dimensional apparatus of the present invention.
Figure 15:
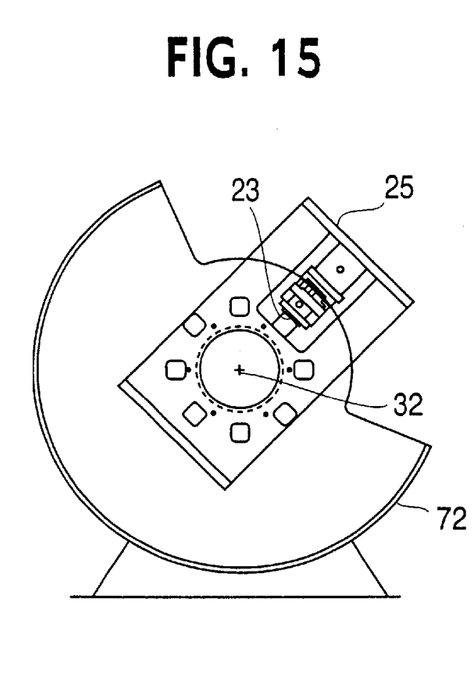
Figure 16:
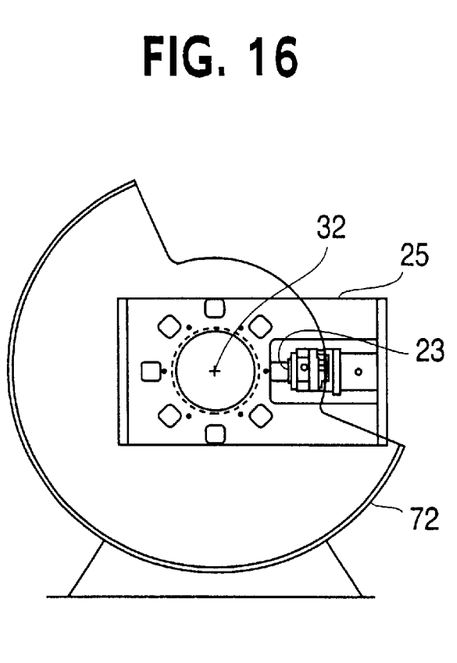
Figure 17:
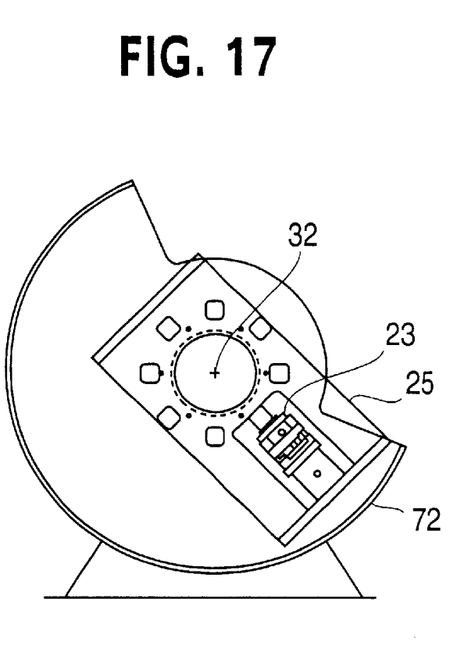

As shown in FIG. 13 of the drawings, the aiming crystals 15 and steering crystals 23 are flexibly mounted by picomotors 21 to the frame 25 to allow for adjustments to the X-ray energy selected which is reliant upon the Bragg angle. Thus, the rotation of the frame 25 controls the positioning of the aiming crystals 15 and the steering crystals 23 to control the rotational location of the set of beta beams 19 and the rotational image of the object 28 that is transferred to the detector 30. The positioning of the frame 25 is controlled by the motor 80. The motor 80 is connected to a ring gear 82 that is mounted through the hub 84 to drive the rotational position of the frame 25.

FIGS. 14–17 show how the frame 25 rotates to different rotational positions about the central axis 32. The central axis 32 extends from the alpha beam 14 and passes through the object 28 and onto the detector 30. This allows for the set of crystals 42 to direct the set of beta beams 19 through different rotational paths thorough the object 28 that is to be imaged.

This device 10 uses two end bearing supports 84 and 86 which support the frame 25 which houses the plurality of crystals 42 for guiding the x-ray beam 14. The structural support 72 is manufactured from a ¼" steel plate with openings for allowing the x-rays to pass through at the various rotational positions. The structural support 72 also provides support for the bearing assembly 84. The bearings (not shown) are standard roller bearing assemblies. The internal frame 25, which rotates within the structural support 72, was designed to allow for multiple image rotational positions to allow for various images to be taken from the object from different angular orientations. It is envisioned that the second end support can replaced with an external bearing support so that a continuous image may be scanned without being blocked by the openings in the frame as shown in the drawings.

The internal frame 25 to structural support 72 rotational position is controlled by a stepping motor 80 with orientation decoder feedback. This decoder feedback gives proper accurate information on the positioning of the x-ray image that is being taken. Another option would be allow for continuous movement of this stepping motor to get a complete scan in one shot of an x-ray beam.

Figure 5:
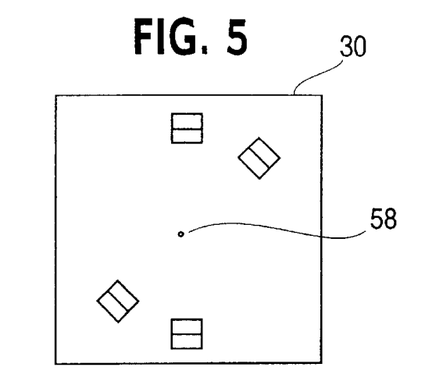
FIG. 5 is a schematic representation of the detector image of FIG. 4 after a linear repositioning of the three-dimensional imaging apparatus.
Figure 6:
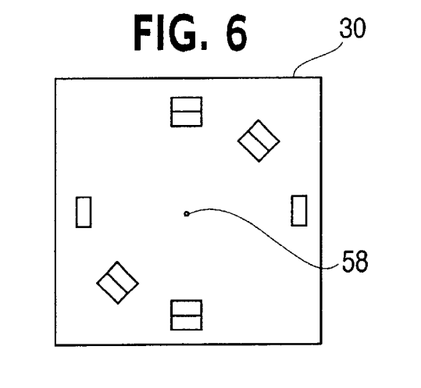
FIG. 6 is a schematic representation of the detector image of FIG. 5 after a rotational repositioning of the three-dimensional imaging apparatus.
Figure 7:
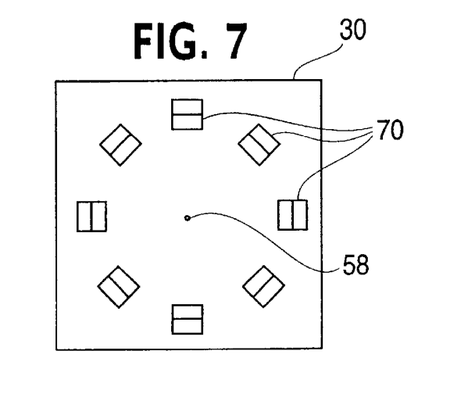
FIG. 7 is a schematic representation of a full scan detector image from the three-dimensional apparatus of the present invention.

Combined Linear and Rotational Positioning Movements:

As shown in FIG. 5, FIG. 6, and FIG. 7, additional linear and rotational positioning of the device 10 will provide a complete three-dimensional image 70 of the object 28 on the detector 30 as an expanded two-dimensional image. Thus, by moving the PLURALITY OF CRYSTALS 42 in the linear manner, and rotating both the set of aiming crystals 15 and the set of steering crystals 23 in a rotational manner, a three dimensional image of the object 28 can be transferred onto the detector 30.

The image produced at each location on the detector during one translation at any given angle is a 2-dimensional representation of the entire volume of the 3-dimensional object as it is seen from a given perspective. Each image is converted to digital data which can then be used as input for volumetric back-projection reconstruction.

Materials Used for the Device:

While some of the x-ray beams will pass through the mosaic crystal, another portion will be absorbed and a third portion will be reflected off of the crystal. Thus, it is sometimes necessary to manufacture or install a lead block in order to prohibit the initial x-ray beam 14 from directly encountering the patient. Because this device uses a fairly intense x-ray beam as the initial beam, it is important that no stray radiation passes through the device and into the patient.

The first aiming crystal 16 and second aiming crystal 18 are formed from pyrolytic graphite which has been repeatedly folded and compressed at high temperature and pressure such that the graphite crystalline planes are randomly oriented creating what is known as a mosaic crystal. All of the crystals 16, 18, 24 and 26 are mounted on adjustable gimbaled frames, which in turn are mounted on motorized linear stages or picomotors 21 to allow for variable alignment of the crystals. The position of the crystals is dependent upon the Bragg angle unique to the energy of the X-rays used for imaging, since the crystals are both angular and energy selective. These picomotors 21 are in turn bolted to the rotating frame 25.

While the present embodiment describes the first aiming crystal 16 and second aiming crystal 18 forming a set of reflective mosaic aiming crystals 19, it is also envisioned that additional crystals could be used to split the alpha beams into additional sections. This could allow for additional views without the rotation of the crystal set on the frame.

The discussion on the mosaic crystals uses the principal of the Bragg angle. The Bragg angle controls the energy that is transmitted off of the mosaic crystal. Thus, the energy that is transferred off of the mosaic crystal is a function of the incoming beam and the angle of the mosaic crystal mirror. This controls the wavelength of the reflected beam according to the type of incoming beam and the angle of the crystal.

In practice, a cylindrical or bent mosaic crystal mirror can be used for both the aiming and steering crystals. This device has been successful with both a first bent mosaic crystal for the initial aiming mirror and a second bent mosaic crystal for the seconding steering mirror. The preferred embodiment only uses a bent mosaic aiming mirror and uses a second straight steering crystal mirror for the present application.

Another alternative embodiment would use a cylindrical aiming mirror to split the initial beam 14 into a circular beam and then use a circular or toroidal style of mosaic crystal mirror to allow for a single beam to form multiple images with one (1) burst of x-ray and energy.

The frame 25 is constructed from rigid aluminum metal and is rotatably positioned by high precision motors and encoders. The frame 25 in turn is supported on a non-rotating base or support structure 72 through an aluminum load bearing support, yoke and precision rotary bearings. Accurate positioning is controlled by software on a computer using feedback from the various motor encoders.

The preferred embodiment was designed for use with objects 28 such as the tissues surrounding the human breast and cancerous tumors within the breast. One of the primary uses of this beam is to develop monochromatic mammography to improve the sensitivity and specificity in diagnosing breast cancer. If the breast or object 28 is imaged using standard techniques, the 3-dimensional information in the breast would be displayed in a 2-dimensional fashion by the film due to projection onto a flat imaging plane. As recently discovered, the cancerous tissues of the breast absorb radiation more avidly that normal tissues by approximately 11%. Unfortunately, small amounts of cancer would image the same as larger amounts of normal tissues on standard films. To unravel the 3-D information, one usually has to move the x-ray beam and/or detector to gain the additional spatial information concerning the part, such as in CT wherein the X-ray tube and detector rotate about the patient in unison or in standard tomography wherein the tube and film move dynamically in opposite directions above and below the patient about a fixed fulcrum point which corresponds to a plane within the patient. Since the beam cannot normally be moved with the FEL, this method for rotation was devised using mosaic crystals for imaging the breast or object 28.

The detector 30 currently in use consists of a fluorescent screen mounted on the front of a light tight box that contains a thermoelectrically cooled CCD camera optically coupled to the images formed on the screen by a standard camera lens. This allows for direct digital acquisition of the various projections.

The central axis 32 is located along the axis of the alpha beam 14. In the preferred embodiment, the central axis 32 passes through the object 28 that is to be imaged. This allows for an easy adjustment of the system and for consistent imaging of objects by the three-dimensional imaging device 10.

The apex 35 of the set of aiming crystals 15 is located on the central axis 32 of the device 10.

In the preferred embodiment, the inverted "V" 36 positions each aiming crystal at a five (5) to seven (7) degree angle off of the central axis 32. The angle here is dictated by the energy selectivity of the mosaic crystal. Each X-ray energy is reflected at a different angle by the crystal. To change the energy to be used for imaging one adjusts the angle of reflectance to match that calculated to conform to Bragg's angle for that energy.

The first image location and second image location are formed on the detector 30 by fluorescence of a standard x-ray screen phosphor when struck by X-rays. The light generated is collected by the lens of the CCD camera and imaged onto the surface of the thermoelectrically cooled thinned backilluminated CCD. This data is clocked out of the CCD in standard fashion following a variable delay for formation of an entire image created during one translation of the entire crystal set at any one fixed rotational angle.

The central rotating point 58 is located at the point where the central axis 32 passes into the detector 30.

The aforementioned descriptions provide the basis for the method of the invention. The method of producing the three-dimensional scan of this invention includes the steps of providing an alpha beam and a detector; splitting the alpha beam to form a split beam or beta beams that can include multiple split beams or multiple beta beams; directing the split beam through an object that is to be imaged, so that the beams continue onto the detector; and recording the image of the object with the detector. The directing of the split beam includes linearly positioning reflective devices or crystals to linearly position the split beam. The directing of the split beam can also include rotationally positioning reflective devices or crystals to rotationally position the split beam. Thus, the present invention can include both linearly and rotationally positioning reflective devices or crystals to properly position the split beam. By custom designing the mosaic crystals to include concave or convex reflecting surfaces, the entire image at any given rotational angle can be obtained at the imaging detector without the need for the translational component at all. Then the various complete angular projections for the entire imaged part can be obtained solely by rotation about the axis of the entire crystal set.

Therefore, although there have been described particular embodiments of the present invention of a new and useful An Apparatus and Method for Three-Dimensional Imaging Using a Stationary Monochromatic X-Ray Beam, it is not intended that such references be construed as limitations upon the scope of this invention except as set forth in the following claims.

What is claimed is:

1. A device for generating a three-dimensional image of an object comprising:
    a beam source projecting a first beam along an axis;
    an aiming crystal located along said axis, wherein said aiming crystal redirects said first beam to form a second beam;
    a steering crystal, wherein said aiming crystal directs said second beam onto said steering crystal; and
    a detector, wherein said steering crystal directs said second beam through said object onto said detector,
    wherein said aiming crystal and said steering crystal are rotated to scan the object around an axis of rotation.

2. The three-dimensional imaging device of claim 1, wherein:
    said steering and aiming are crystal linearly positioned to linearly scan the object.

3. The three-dimensional imaging device of claim 1, wherein:
    said axis of rotation is concentric with an axis of said first beam.

4. The three-dimensional imaging device of claim 1, wherein:
    said beam source includes a monochromatic beam source.

5. The three-dimensional imaging device of claim 1, wherein:
    said beam source includes a stationary beam source.

6. The three-dimensional imaging device of claim 1, wherein:
    said aiming crystal includes a mosaic reflective crystal.

7. The three-dimensional imaging device of claim 1, wherein:
    said aiming crystal includes an apex.

8. The three-dimensional imaging device of claim 1, wherein:
    said steering crystal includes a mosaic reflective crystal.

9. The three-dimensional imaging device of claim 1, wherein:
    said second beam is positioned to converge on said object from different locations.

10. The three-dimensional imaging device of claim 1, wherein:
    said detector is a stationary detector.

11. A method of producing a three-dimensional scan of an object, comprising:
    providing an alpha beam;
    providing a detector;
    splitting said alpha beam to form a split beam;
    directing said split beam through said object and onto said detector;
    recording an image of said object with said detector,
    wherein said directing said split beam includes linearly and rotationally positioning reflective devices.

12. An imaging device comprising:
    a substantially stationary beam source that projects a first beam along a primary axis;
    a first crystal that is located on the primary axis and that redirects at least a portion of the first beam to form a second beam;
    a second crystal that receives the second beam and redirects at least a portion of the second beam through a substantially stationary object to be imaged; and
    a substantially stationary detector that receives a transmitted portion of the second beam portion,
    wherein the first and second crystals operate together to redirect the second beam portion through the object from a plurality of perspectives, such that the transmitted portion of the second beam portion strikes the detector at a plurality of positions corresponding to the plurality of perspectives,
    whereby a three-dimensional image of at least a portion of the object is generated using information collected by the detector.

13. The imaging device of claim 12, wherein the first and second crystals are synchronously moved to direct the first and second beams in a desired manner from the beam source, through the object and onto the detector.

14. The imaging device of claim 13, wherein the first and second crystals are mounted on a movable frame.

15. The imaging device of claim 14, wherein the frame, and thereby the first and second crystals, moves along the primary axis, so as to scan the second beam through linearly successive portions of the object, whereby the detector detects information on each of the linearly successive portions.

16. The imaging device of claim 15, wherein the frame, and thereby the first and second crystals, rotates in unison around the primary axis, so as to scan the second beam through rotationally successive portions of the object, whereby the detector detects each of the rotationally successive portions.

17. The imaging device of claim 16, wherein the movements of the frame along and around the primary axis are performed discretely, so that three-dimensional images of separate portions of the object are obtained individually.

18. The imaging device of claim 16, wherein the movements of the frame along and around the primary axis are performed continuously, the three-dimensional image is obtained in a single exposure of the first beam.

19. The imaging device of claim 14, wherein the frame, and thereby the first and second crystals, rotates in unison around the primary axis, so as to scan the second beam through rotationally successive portions of the object, whereby the detector detects each of the rotationally successive portions.

20. The imaging device of claim 19, wherein a size and shape of the second beam and a corresponding size and shape of the second crystal are such that a cross section of the object that is approximately perpendicular to the detector is entirely detected by the detector during a single exposure of the first beam.

21. The imaging device of claim 20, further comprising a plurality of second crystals arranged substantially equidistant from the primary axis, wherein the first crystal splits the first beam to form multiple beams in a substantially circular pattern, whereby the substantially stationary detector detects a cross section of the substantially stationary object that is approximately parallel to the detector.

22. The imaging device of claim 12, further comprising a plurality of second crystals arranged substantially equidistant from the primary axis, wherein the first crystal or a plurality of first crystals splits the first beam such that the second beam is substantially circular in shape, whereby, during a single exposure of the first beam, the detector detects a cross section of the object that is approximately parallel to the detector.

23. The imaging device of claim 22, wherein a size and shape of the second beam and a corresponding size and shape of the second crystal are such that a cross section of the object that is approximately perpendicular to the detector is entirely detected by the detector during a single exposure of the first beam.

24. The imaging device of claim 12, wherein the first and second crystals are mosaic crystals.

25. The imaging device of claim 24, wherein the first crystal is a bent mosaic crystal and the second crystal is a straight mosaic crystal.

26. The imaging device of claim 12, wherein the object is located along the primary axis.

27. The imaging device of claim 12, further comprising:
a plurality of first crystals that are located along the primary axis and approximately equidistant from the beam source; and
a plurality of second crystals that are located between the first crystals and the object,
wherein the first beam is split into a plurality of second beams by the plurality of first crystals, the plurality of second beams each being directed to a corresponding one of the plurality of second crystals and thereby directed to each converge upon a target point within the object.

28. An imaging device comprising:
a beam source that projects an x-ray beam along a primary axis;
a frame comprising a crystal set that receives the x-ray beam and redirects it onto an object to be imaged; and
a detector that detects a position and intensity of portions of the x-ray beam that travel through the object and impinge thereon,
wherein the crystal set within the frame redirects the x-ray beam so that portions of the x-ray beam impinge upon the object from a plurality of angles and positions, whereby the detector detects information from a which a three-dimensional image of at least a portion of the object is obtained.

29. The imaging device of claim 28, wherein the beam source, object and detector are substantially stationary during imaging.

30. The imaging device of claim 28, wherein the three-dimensional image comprises linear and rotational imaging information on the object.

31. The imaging device of claim 30, wherein the linear imaging information is obtained by moving the frame along the primary axis while the x-ray beam is being produced by the beam source.

32. The imaging device of claim 30, wherein the rotational imaging information is obtained by rotating the frame about the primary axis.

33. The imaging device of claim 30, wherein the crystal set splits the x-ray beam into a plurality of secondary x-ray beams, and wherein the plurality of secondary x-ray beams converge upon an imaging point within the object.

34. An imaging method, comprising:
generating an x-ray beam from a beam source along a primary axis;
directing the x-ray beam away from the primary axis;
re-directing the x-ray beam through an object to be imaged from a plurality of perspectives;
detecting a portion of the x-ray beam that is transmitted through the object from each of the plurality of perspectives, using a detector; and
generating a three-dimensional image of the object based on information obtained by the detector.

35. The method of claim 34, wherein said directing the x-ray beam away from the primary axis further comprises:
directing the x-ray beam onto at least a first crystal,
and further wherein said re-directing the x-ray beam through an object to be imaged from a plurality of perspectives further comprises:
redirecting the x-ray beam onto at least a second crystal.

36. The method of claim 35, wherein the at least a first crystal comprises a plurality of primary crystal surfaces, and further wherein said directing the x-ray beam onto at least a first crystal further comprises:
splitting the x-ray beam into a plurality of secondary x-ray beams using the plurality of primary crystal surfaces.

37. The method of claim 36, wherein the at least a second crystal comprises a plurality of secondary crystal surfaces, and further wherein said redirecting at least a portion of the x-ray beam onto at least a second crystal further comprises:
redirecting the plurality of secondary x-ray beams using the plurality of secondary crystal surfaces.

38. The method of claim 37, wherein said redirecting the plurality of secondary x-ray beams using the plurality of secondary crystal surfaces further comprises:

converging the plurality of secondary x-ray beams upon a single imaging point within the object.

39. The method of claim 34, wherein the at least a first and second crystal are contained within, and attached to, a movable frame.

40. The method of claim 39, wherein said redirecting at least a portion of the x-ray beam onto at least a portion of a substantially stationary object to be imaged further comprises:

moving the frame along the primary axis, so as to obtain linear imaging information on the object.

41. The method of claim 39, wherein said re directing at least a portion of the x-ray beam onto at least a portion of a substantially stationary object to be imaged further comprises:

rotating the frame about the primary axis, so as to obtain rotational imaging information on the object.

42. The method of claim 34, wherein the beam source, object and detector are substantially stationary.

43. A three-dimensional imaging system, comprising:

a beam source that generates an x-ray beam along a primary axis;

means for directing the x-ray beam through an object to be imaged from a plurality of angles; and a detector that detects a portion of the x-ray beam that is transmitted through the object to be imaged from the plurality of angles and generates a three-dimensional image of the object therefrom.

44. The system of claim 43, wherein the means for directing the x-ray beam further comprises:

a first means for directing the x-ray beam away from the primary axis; and a second means for re-directing the x-ray beam through the object.

45. The system of claim 43, wherein the beam source, object and detector are substantially stationary during an imaging process.

* * * * *